(12) United States Patent
Treco et al.

(10) Patent No.: US 6,537,542 B1
(45) Date of Patent: *Mar. 25, 2003

(54) TARGETED INTRODUCTION OF DNA INTO PRIMARY OR SECONDARY CELLS AND THEIR USE FOR GENE THERAPY AND PROTEIN PRODUCTION

(75) Inventors: Douglas Treco, Arlington; Michael W. Heartlein, Boxborough; Richard F Selden, Wellesley, all of MA (US)

(73) Assignee: Transkaryotic Therapies, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,697

(22) Filed: Apr. 14, 2000

Related U.S. Application Data

(63) Continuation of application No. 08/446,921, filed on May 18, 1995, now Pat. No. 6,187,305, which is a division of application No. 08/231,439, filed on Apr. 20, 1994, now Pat. No. 6,063,630, which is a continuation of application No. 07/789,188, filed on Nov. 5, 1991, now abandoned.

(51) Int. Cl.⁷ .......................... A61K 48/00; C12N 15/00
(52) U.S. Cl. ................. 424/93.21; 424/93.1; 424/93.2; 514/44; 435/455
(58) Field of Search .............................. 800/3, 8, 9, 11, 800/13, 18; 424/93.21; 514/44; 435/325

(56) References Cited

U.S. PATENT DOCUMENTS

| | | | |
|---|---|---|---|
| 4,396,601 A | 8/1983 | Salser et al. | 424/94.5 |
| 4,497,796 A | 2/1985 | Salser et al. | 514/44 |
| 4,789,550 A | 12/1988 | Hommel et al. | 424/493 |
| 4,892,538 A | 1/1990 | Aebischer et al. | 604/891.1 |
| 4,980,286 A | 12/1990 | Morgan et al. | 435/371 |
| 5,082,670 A | 1/1992 | Gage et al. | 424/520 |
| 5,089,397 A | 2/1992 | Kushner et al. | 435/69.7 |
| 5,166,059 A | 11/1992 | Pastan et al. | 435/69.7 |
| 5,175,255 A | 12/1992 | Thomason et al. | 530/380 |
| 5,194,596 A | 3/1993 | Tischer et al. | 530/399 |
| 5,219,740 A | 6/1993 | Miller et al. | 435/69.6 |
| 5,272,071 A | 12/1993 | Chappel | 435/6 |
| 5,399,346 A | 3/1995 | Anderson et al. | 424/93.21 |
| 5,460,959 A | 10/1995 | Mulligan et al. | 435/456 |
| 5,464,764 A | 11/1995 | Capecchi et al. | 435/6 |
| 5,578,461 A | 11/1996 | Sherwin et al. | 435/69.1 |

(List continued on next page.)

FOREIGN PATENT DOCUMENTS

| | | |
|---|---|---|
| EP | 0038765 | 3/1981 |
| EP | 0236059 | 9/1987 |
| EP | 0255231 | 2/1988 |
| EP | 0289034 | 11/1988 |
| EP | 0452894 | 10/1991 |
| GB | 2159172 | 11/1985 |
| WO | WO 87/00201 | 1/1987 |
| WO | WO 89/05345 | 12/1987 |
| WO | WO 88/00239 | 1/1988 |
| WO | WO 89/07136 | 2/1988 |
| WO | WO 88/08306 | 3/1988 |
| WO | WO 90/06997 | 12/1988 |
| WO | WO 89/01517 | 2/1989 |
| WO | WO 90/12878 | 5/1989 |
| WO | WO 90/15863 | 6/1989 |
| WO | WO 90/06757 | 6/1990 |
| WO | WO 90/11354 | 10/1990 |

(List continued on next page.)

OTHER PUBLICATIONS

Ledley; Clinical Consideration, 1991, Human Gene Therapy 2: 77–83.*
Eck et. al.; Gene–Based Therapy, 1996, Pharmacological Basis of Therapeutics: 77–101.*
Chang et. al.; Autologous fibroblast Implantation, 1990, Mol. Biol. Med. 7: 461–470.*
Chang et. al.; Modification of DNA ends can decrease end joining relative to homologous recombination in mammalian cells, 1987, Proc. Natl. Acad. vol. 84: 4959–4963.*
Mes–Masson et. al.; Expression of oncomodulin does not lead to the transformation of immortalization of mammalian cells in vitro, 1989, Journal of Cell Science 94: 517–525.*
EP Opposition Apr. 30, 1998, On behalf of Genetic Therapy, Inc.
EP Opposition Apr. 30, 1998, On behalf of Institut Pasteur.
EP Opposition May 4, 1998, On behalf of Boehringer Mannheim GMBH.
EP Opposition May 4, 1998, On behalf of Applied Research Systems.
EP Opposition May 4, 1998, On behalf of Cell Genesys, Inc.
Alberts, Molecular Biology of the Cell (Glossary), third edition, Garland Publishing, Inc., New York.
Antin et al., "Single Cell Analysis of Transfected Gene Expression in Primary Heart Cultures Containing Multiple Cell Types," BioTechniques 6:640–648, 1988.
Barr et al., "Systemic Delivery of Recombinant Proteins by Genetically Modified Myoblasts, " Science, 254:1507–1509, 1991.

Primary Examiner—Deborah Crouch
Assistant Examiner—Thaian N. Ton
(74) Attorney, Agent, or Firm—Clark & Elbing LLP

(57) ABSTRACT

The present invention relates to a method of gene or DNA targeting in cells of vertebrate, particularly mammalian, origin. That is, it relates to a method of introducing DNA into primary or secondary cells of vertebrate origin through homologous recombination or targeting of the DNA, which is introduced into genomic DNA of the primary or secondary cells at a preselected site. The present invention further relates to primary or secondary cells, referred to as homologously recombinant (HR) primary or secondary cells, produced by the present method and to uses of the homologously recombinant primary or secondary cells. The present invention also relates to a method of turning on a gene present in primary cells, secondary cells or immortalized cells of vertebrate origin, which is normally not expressed in the cells or is not expressed at significant levels in the cells.

11 Claims, 2 Drawing Sheets

U.S. PATENT DOCUMENTS

| | | | | |
|---|---|---|---|---|
| 5,733,761 A | * | 3/1998 | Treco et al. | 435/172.3 |
| 5,789,215 A | | 8/1998 | Berns et al. | 800/25 |
| 5,968,502 A | * | 10/1999 | Treco et al. | 424/93.21 |
| 5,994,127 A | | 11/1999 | Selden et al. | 435/325 |
| 6,048,524 A | | 4/2000 | Selden et al. | 424/93.21 |
| 6,048,724 A | | 4/2000 | Selden et al. | 435/325 |
| 6,048,729 A | | 4/2000 | Selden et al. | 435/455 |
| 6,054,288 A | | 4/2000 | Selden et al. | 435/69.1 |
| 6,063,630 A | | 5/2000 | Treco et al. | 435/463 |
| 6,187,305 B1 | | 2/2001 | Treco et al. | 424/93.21 |
| 6,214,622 B1 | * | 4/2001 | Treco et al. | 435/463 |

FOREIGN PATENT DOCUMENTS

| | | |
|---|---|---|
| WO | WO 92/07573 | 10/1990 |
| WO | WO 92/12242 | 12/1990 |
| WO | WO 92/15676 | 3/1991 |
| WO | WO 91/06666 | 5/1991 |
| WO | WO 91/06667 | 5/1991 |
| WO | WO 91/09955 | 7/1991 |
| WO | WO 91/13151 | 9/1991 |
| WO | WO 91/19796 | 12/1991 |
| WO | WO 92/03917 | 3/1992 |
| WO | WO 92/08796 | 3/1992 |
| WO | WO 92/19255 | 11/1992 |
| WO | WO 92/20808 | 11/1992 |
| WO | WO 93/04169 | 3/1993 |

OTHER PUBLICATIONS

Behr et al., "Efficient Gene Transfer Into Mammalian Primary Endocrine Cells with Lipopolyamine–coated DNA," Proceedings of the National Academy of Sciences U.S.A. 86:6982–6986, 1989.

Bennett et al., "A Role for Cyclosporin A in Gene Replacement Therapy," American Journal of Human Genetics 45:A109, 1989.

Bennett et al., "Suppression of Immunological Response Against a Novel Gene Product Delivered by Implants of Genetically Modified Fibroblasts," Molecular Biology and Medicine, 7:471–477, 1990.

Boggs, "Targeted Gene Modification for Gene Therapy of Stem Cells," International Journal of Cell Cloning 8:80–96, 1990.

Brash et al., "Strontium Phosphate Transfection of Human Cells in Primary Culture: Stable Expression of the Simian Virus 40 Large–T–Antigen Gene in Primary Human Bronchial Epithelial Cells," Molecular and Cellular Biology 7(5):2031–2034, 1987.

Brenner et al., "Expression of Collagen Genes in the Liver," Molecular Biology and Medicine 7:105–115, 1990.

Brigham et al., "Expression of a Prokaryotic Gene in Cultured Lung Endothelial Cells after Lipofection with a Plasmid Vector," Am. Journal of Respiratory Cell. and Molecular Biology 1:95–100, 1989.

Burrin et al., "Regulation of Transfected Glycoprotein Hormone α–Gene Expression in Primary Pituitary Cell Cultures," Molecular Endocrinology 3(10):1643–1651, 1989.

Camerini–Otero, "Right on Target," The New Biologist 2:337–341, 1990.

Cann et al., "High Efficiency Transfection of Primary Human Lymphocytes and Studies of Gene Expression," Oncogene 3:123–128, 1988.

Capecchi, "High Efficiency Transformation By Direct Microinjection of DNA Into Cultured Mammalian Cells," Cell 22:479–488, 1980.

Capecchi, "The New Mouse Genetics: Altering the Genome by Gene Targeting," Trends in Genetics 5:70–76, 1989.

Capecchi, "Altering the Genome by Homologous Recombination," Science 244:1288–1292, 1989.

Chang et al., "High Efficiency Gene Transfection by Electroporation Using a Radio–Frequency Electric Field," Biochimica et Biophysica Acta, 1092:153–160, 1991.

Chang et al., "Autologous Fibroblast Implantation Feasibility and Potential Problems in Gene Replacement Therapy," Molecular Biology and Medicine, 7:461–470, 1990.

Cline, "Perspectives for Gene Therapy: Inserting New Genetic Information into Mammalian Cells by Physical Techniques and Viral Vectors," Pharmacology and Therapy 29:69–92, 1985.

Corey et al., "Erythropoiesis in Murine Long–Term Marrow Cultures Following Transfer of the Erythropoietin cDNA into Marrow Stromal Cells," Experimental Hematology, 18(3):201–204, 1990.

Crystal, "Transfer of Genes to Humans: Early Lessons and Obstacles to Success," Science 270:404–410, 1995.

Daubas et al., "Functional Activity of the Two Promoters of the Myosin Alkali Light Chain Gene in Primary Muscle Cell Cultures: Comparison with Other Muscle Gene Promoters and Other Culture Systems," Nucleic Acids Research 16(4):1251–1271, 1988.

Dhawan et al., "Systemic Delivery of Human Growth Hormone by Injection of Genetically Engineered Myoblasts," Science 254:1509–1512, 1991.

Diatloff–Zito et al., "Abnormal Response to DNA Crosslinking Agents of Fanconi Anemia Fibroblasts can be Corrected by Transfection with Normal Human DNA," Proceedings of the National Academy of Sciences U.S.A. 83:7034–7038, 1986.

Doering et al., "Expression of a Novel Gene Product by Transplants of Genetically Modified Primary Fibroblasts in the Central Nervous Systems," Journal of Neuroscience Research 29:292–298, 1991.

Doetschman et al., "Targeted Correction of a Mutant HPRT Gene in Mouse Embryonic Stem Cells," Nature, 330:576–578, 1987.

Doetschman et al., "Targeted Mutation of the HPRT Gene in Mouse Embryonic Stem Cells," Proceedings of the National Academy of Sciences U.S.A. 85:8583–8587, 1988.

Drucker, et al., "Cell–Specific Post–Translational Procesing of Preproglucagon Expressed from a Metallothionein–Glucagon Fusion Gene," The Journal of Biological Chemistry 261(21):9637–9643, 1986.

Duncan et al., Biochemistry (Moscow) 62:1263–1274, 1997.

Finn et al., "Homologous Plasmid Recombination is Elevated in Immortally Transformed Cells," Molecular and Cellular Biology, 9:4009–4017, 1989.

Fishel et al., "Biochemical Studies of Homologous and Nonhomologous Recombination in Human Cells," Biochimie, 73:257–267, 1991.

Fountain et al., "Transfection of Primary Human Skin Fibroblasts by Electroporation," Gene 68:(1):167–172, 1988.

Friedmann, "Progress Toward Human Gene Therapy," Science 244:1275–1281, 1989.

Frohman, "Cut, Paste, and Save: New Approaches to Altering Specific Gene in Mice," Cell 56:145–147, 1989.

Gao et al., "A Novel Cationic Liposome Reagent for Efficient Transfection of Mammalian Cells," Biochemical and Biophysical Research Communications 179(1):280–285, 1995.

Gareis et al., "Homologous Recombination of Exogenous DNA Fragments with Genomic DNA in Somatic Cells of Mice," Cellular and Modecular Biology 37(2):191–203, 1991.

Ginot et al., "Transfection of Hepatic Genes Into Adult Rat Hepatocytes in Primary Culture and Their Tissue–Specific Expression," European Journal of Biochemistry 180:289–294, 1989.

Glover, "Expression of Cloned Genes in Animal Cells," In "Gene Cloning, The Mechanics of DNA Manipulation," pp. 179–202, Chapman and Hall, New York, 1984.

Hammer et al., "Partial Correction of Murine Hereditary Growth Disorder by Germ–Line Incorporation of a New Gene," Nature 311:65–67, 1984.

Harper et al., "Expression of Transfected DNA by Primary Murine Keratinocytes," Journal of Investigative Dermatology 91(2):150–153, 1988.

Heartlein et al., "Long–Term Production and Delivery of Human Growth Hormone," Proceedings of the National Academy of Sciences U.S.A. 91:10967–10971, 1994.

Hesse et al., "Regulated Gene Expression in Transfected Primary Chicken Erythrocytes," Proceedings of the National Academy of Sciences U.S.A. 83:4312–4316, 1986.

Iannuzzi et al., "The Introduction of Biologically Active Foreign Genes into Human Respiratory Epithelial Cells Using Electroporation," Am. Rev. of Resp. Dis. 138:965–968, 1988.

Imagawa et al., "Regulatory Elements of the Erythropoietin Gene," Blood 77(2):278–285, 1991.

Itzhaki et al., "Targeted Disruption of a Human Interferon –Inducible Gene Detected by Secretion of Human Growth Hormone," Nucleic Acids Research 19(4):3835–3842, 1991.

Jensen et al., "High–Frequency Transfection of Cultured Human Epidermal Basal Cells That Differentiate to Form a Multilayered Tissue," Experimental Cell Research 189:163–168, 1990.

Joyner et al., "Production of a mutation in mouse En–2 gene by homologous recombination in embryonic stem cells," Nature 338:153–155, 1989.

Kaufman et al., "Strategies for Obtaining High Level Expression in Mammalian Cells," Technique 2:221–236, 1990.

Keating et al., "Gene Transfer by Electroporation: A Model for Gene Therapy," Progress in Clinical Biological Research 333:491–498, 1990.

Keating et al., "Effect of Different Promoters on Expression Genes Introduced Into Hematopoietic and Marrow Stromal Cells by Electroporation," Experimental Hematology 18:99–102, 1990.

Kendrew, The Encyclopedia of Molecular Biology, Blackwell Science Ltd., Oxford, p. 1085, 1994.

Kramerova et al., "Expression of the Cloned Human Erythropoietin Gene in CHO Cells," Biopolim Kletka 5(2):47–51, 1989.

Kremer et al., "Regulation of Parathyroid Hormone–like Peptide in Cultured Normal Human Keratinocytes," The Journal of Clinical Investigation 87:884–893, 1991.

Kreymann et al., "Glucagon–Like Peptide–1 7–36: A Physiological Incretin In Man," The Lancet 2:1300–1304, 1987.

Kriegler, "Gene Transfer and Expression: A Laboratory Manual," Stockton Press, New York, 1990.

Le Mouellic et al., "Targeted Replacement of the Homeobox Gene Hox 3.1 by the *Escherichia coli* lacZ in Mouse Chimeric Embryos," Proceedings of the National Academy of Sciences U.S.A. 87:4712–4716, 1990.

Ledley, "Clinical Considerations in the Design of Protocols for Somatic Gene Therapy," Human Gene Therapy 2:77–83, 1991.

Lee et al., "Glucagon Gene 3'–Flanking Sequences Direct Formation of Proglucagon Messenger RNA 3'–Ends in Islet and Nonislet Cells Lines," Molecular Endocrinology, 4(6):800–806, 1990.

Lewin, Genes IV, Oxford University Press, Oxford, p. 820, 1990.

Litwer et al., "Reversion of the Maple Syrup Urine Disease Phenotype of Impaired Branched Chain Alpha–Ketoacid Dehydrogenase Complex Activity in Fibroblasts from an Affected Child," The Journal of Biological Chemistry 264:14597–14600, 1989.

Loeffler et al., "Lipopolyamine–Mediated Transfection Allows Gene Expression Studies in Primary Neuronal Cells," Journal of Neurochemistry 54:1812–1815, 1990.

Lu et al., "Gene Transfer by Lipofection in Rabbit and Human Secretory Epithelial Cells," Pflügers Archives 415:198–203, 1989.

Lupton et al., "Dominant Positive and Negative Selection Using A Hygromycin Phosphotransferase–Thymidine Kinase Fusion Gene," Molecular and Cellular Biology 11(6):3374–3378, 1991.

Mansour, "Gene Targeting in Murine Embryonic Stem Cells: Introduction of Specific Alterations into the Mammalian Genome," Genet. Anal. Tech Appl. 7:219–227, 1990.

Mansour et al., "Disruption of the Proto–Oncogene int–2 in Mouse Embryo–Derived Stem Cells: A General Strategy for Targeting Mutations to Non–Selectable Genes," Nature 336:348–352, 1988.

Marshall, "Gene Therapy's Growing Pains," Science 269:1050–1055, 1995.

Mercola et al., "Insertion of New Genetic Information into Bone Marrow Cells of Mice: Comparison of Two Selectable Genes," Annals New York Academy of Sciences, p. 272–280, 1982.

Mes–Masson et al., "Expression of Oncomodulin Does Not Lead to the Transformation or Immortalization of Mammalian Cells In Vitro," Journal of Cellular Science, 94:517–25, 1989.

Morgan et al., "Expression of an Exogenous Growth Hormone Gene by Transplantable Human Epidermal Cells," Science 237:1476–1479, 1987.

Morgenstern et al., "Advanced Mammalian Gene Transfer: High Titre Retroviral With Multiple Drug Selection Markers and a Complementary Helper–Free Packaging Cell Line," Nucleic Acids Research 18(12):3587–3596, 1990.

Narayanan et al., "In Vivo Expression of a Nonselected Gene Transferred into Murine Hematopoietic Stem Cells by Electroporation," Biochemical and Biophysical Research Communications 141:1018–1024, 1986.

Ogura et al., "Implantation of Genetically Manipulated Fibroblasts into Mice as Antitumor α–Interferon Therapy," Cancer Research 50:5102–5106, 1990.

Orkin et al., "Report and Recommendations of the Panel to Assess the NIH Investment in Research on Gene Therapy," 1995.

Palmer et al., "Gentically Modified Skin Fibroblasts Persist Long After Transplantation But Gradually Inactivate Introduced Genes," Proceedings of the National Academy of Sciences U.S.A. 88:1330–1334, 1991.

Palmiter et al., "Metallothionein–Human GH Fusion Genes Stimulate Growth of Mice," Science 222:809–814, 1983.

Pasco et al., "Laboratory Methods, Efficient DNA–Mediated Gene Transfer into Primary Cultures of Adult Rat Hepatocytes," DNA 8(7):535–541, 1989.

Ponder et al., "Evaluation of Relative Promoter Strength in Primary Hepatocytes Using Optimized Lipofection," Human Gene Therapy 2:41–52, 1991.

Ponticelli et al., "Correction of Anaemia with Recombinant Human Erythropoietin," Nephron 52:201–208, 1989.

Potter, "Electroporation in Biology: Methods, Applications, and Instrumentation," Analytical Biochemistry 174:361–73, 1988.

Powell, "Human Erythropoietin Gene: High Level Expression In Stably Transfected Mammalian Cells and Chromosome Localization," Proceedings of the National Academy of Sciences U.S.A. 83:6465–6469, 1986.

Rippe et al., "DNA–Mediated Gene Transfer Into Adult Rat Hepatocytes in Primary Culture," Molecular and Cellular Biology 10(2):689–695, 1990.

Robertson, "Using Embryonic Stem Cells to Introduce Mutations into the Mouse Germ Line," Biology of Reproduction 44:238–245, 1991.

Rodriguez et al., "Recombinant DNA Techniques: An Introduction," The Benjamin/Cummings Publishing Company, Inc., London, 1983.

Rosenfeld et al., "In Vivo Transfer of the Human Cystic Fibrosis Transmembrane Conductance Regulator Gene to the Airway Epithelium," Cell 68:143–155, 1992.

Sambrook et al., "Molecular Cloning," Cold Spring Harbor Laboratory Press, Cold Spring Harbor, New York, p. 16.3–16.4, 1989.

Sandhu et al., "Human Gene Therapy," Critical Reviews in Biotechnology 17:307–326, 1997.

Scharfmann et al., "Long–Term In Vivo Expression of Retrovirus–Mediated Gene Transfer in Mouse Fibroblast Implants," Proceedings of the National Academy of Sciences U.S.A. 88:4626–4630, 1991.

Sedivy et al., "Positive Genetic Selection for Gene Disruption in Mammalian Cells by Homologous Recombination," Proceedings of the National Academy of Sciences U.S.A. 86:227–231, 1989.

Selden et al., "Regulation of Insulin–Gene Expression," The New England Journal of Medicine 317:1067–1076, 1987.

Selden et al., "Implantation of Genetically Engineered Fibroblasts into Mice: Implications for Gene Therapy," Science 236:714–718, 1987.

Shesely et al., "Correction of a Human $\beta^s$–globin Gene by Gene Targeting," Proceedings of the National Academy of Sciences U.S.A. 88:4294–4298, 1991.

Sittler et al., "Tissue–Specific Expression of the Rat Growth Hormone Gene is Due to the Interaction of Multiple Promoter, Not Enhancer, Elements," DNA and Cell Biology 9(7):511–518, 1990.

Smith, "Regulation of Hematopoiesis," The Yale Journal of Biology and Medicine, 63(5):371–80, 1990.

Spandidos, "Electric Field–Mediated Gene Transfer (Electroporation) into Mouse Friend and Human K562 Erythroleukemic Cells," Gene Anal. Tech., 4:50–56, 1987.

Stacey et al., "Electroporation and DNA–Dependent Cell Death in Murine Macrophages," Immunology and Cell Biology 71:75–85, 1993.

St. Louis et al., "An Alternative Approach to Somatic Cell Gene Therapy," Proceedings of the National Academy of Sciences U.S.A., 85:3150–3154, 1988.

Tatsuka et al., "An Improved Method of Electroporation for Introducing Biologically Active Foreign Genes Into Cultured Mammalian Cells," Experimental Cell Research 178:154–162, 1988.

Thomas et al., "Site–Directed Mutagenesis by Gene Targeting in Mouse Embryo–Derived Stem Cells," Cell 51:503–512, 1987.

Thomas et al., "Targeted Disruption of the Murine int–1 Proto–oncogene Resulting in Severe Abnormalities in Midbrain and Cerebellar Development," Nature 346:847–850, 1990.

Thompson et al., "Germ Line Transmission and Expression of a Corrected HPRT Gene Produced by Gene Targeting in Embryonic Stem Cells," Cell 56:313–321, 1989.

Toneguzzo et al., "Stable Expression of Selectable Genes Introduced into Human Hematopoietic Stem Cells by Electric Field–Mediated DNA Transfer," Proceedings of the National Academy of Sciences U.S.A. 83:3496–3499, 1986.

Treco et al., "Non–Viral Gene Therapy," Molecular Medicine Today 1:314–321, 1995.

Treco et al., "Fibroblast Cell Biology and Gene Therapy," Somatic Gene Therapy, ISBN 0–8493–2440–8:49–60, 1995.

Tur–Kaspa et al., "Use of Electroporation to Introduce Biologically Active Foreign Genes Into Primary Rat Hepatocytes," Molecular and Cellular Biology 6:716–718, 1986.

Vega, "Prospects for Homologous Recombination in Human Gene Therapy," Human Genetics 87:245–253, 1991.

Verma, "Gene Therapy," Scientific American, 68–84, Nov., 1990.

Vogelstein et al., "The Multistep Nature of Cancer," Trends in Genetics 9(4):138–141, 1993.

Weatherall, "Scope and Limitations of Gene Therapy," British Medical Bulletin 51:1–11, 1995.

Weidle et al., "A New Expression System for Mammalian Cells Based on Putative Replicator Sequences of the Mouse and a Truncated Thymidine Kinase Gene," Gen 73:427–437, 1988.

Werner et al., "Expression of Transfected Genes by Differentiated, Postmitotic Neurons and Photoreceptors in Primary Cell Cultures," The Journal of Neuroscience Research 25:50–57, 1990.

Wolff et al., "Direct Gene Transfer Into Mouse Muscle In Vivo," Science 247:1465–1468, 1990.

Wu, "Receptor–Mediated Gene Delivery In Vivo," The Journal of Biological Chemistry 266(22):14338–14342, 1991.

Yang et al.,"In Vivo and In Vitro Gene Transfer to Mammalian Somatic Cells by Particle Bombardment," Proceedings of the National Academy of Sciences U.S.A. 87:9568–9572, 1990.

Zheng et al. "Primary cells and established cell lines join DNA ends with the same efficiency relative to homologous recombination," Plasmid 22:99–105, 1989.

Zheng et al., "Fidelity of Targeted Recombination in Human Fibroblasts and Murine Embryonic Stem Cells," Proceedings of the National Academy of Sciences 88:8067–8071, 1991.

U.S. Ser. No. 09/328,130, filed Jun. 8, 1999.

U.S. Ser. No. 09/354,853, filed Jul. 16, 1999.
U.S. Ser. No. 09/374,669, filed Aug. 16, 1999.
U.S. Ser. No. 09/420,861, filed Oct. 19, 1999.
U.S. Ser. No. 09/431,821, filed Nov. 2, 1999.
U.S. Ser. No. 09/545,960, filed Apr. 10, 2000.

U.S. Ser. No. 09/549,200, filed Apr. 13, 2000.

U.S. Ser. No. 09/552,709, filed Apr. 19, 2000.

* cited by examiner

TARGETED INTRODUCTION OF DNA INTO PRIMARY OR SECONDARY CELLS AND THEIR USE FOR GENE THERAPY AND PROTEIN PRODUCTION

This is a continuation of U.S. Ser. No. 08/446,921, filed May 18, 1995, now U.S. Pat. No. 6,187,305 which is a divisional of U.S. Ser. No. 08/231,439, filed Apr. 20, 1994, Now U.S. Pat. No. 6,063,630 which is a continuation of U.S. Ser. No. 07/789,188, filed Nov. 5, 1991 now abandoned.

BACKGROUND OF THE INVENTION

The ability to move DNA from one cell to another is a powerful tool in modern molecular biology, yet the idea that this movement might be possible predates the current revolution in genetic engineering. In 1928, Griffith paved the way for the discovery that nucleic acids are the genetic material when he noticed that the virulence of bacteria could be altered by mixing live bacteria with solutions derived from killed bacteria. By the early 1960's, not only was the structure of the relevant component of the solution, DNA, solved, but it was already established that DNA could be moved into mammalian cells (Syzbalski, 1961). The focus of these early days of molecular biology and tissue culture were irreversibly changed by two critical developments: the discovery of calcium phosphate precipitation, a simple procedure to introduce DNA into immortalized cells in culture (Graham and van der Eb, 1972) and the isolation and characterization of mammalian globin., insulin, and growth hormone genes in the mid- to-late 1970's.

Today, the ability to manipulate DNA and to introduce it into cells has profound practical implications for human health. Recombinant proteins produced by such manipulations are becoming widely accepted treatments for a number of human diseases and play major roles in agriculture. Though far less developed, the field of human gene therapy also has been and will continue to be influenced by improvements in technologies for the manipulation of DNA.

Gene-therapy is a medical intervention in which a small number of the patient's cells are modified genetically to treat or cure any condition, regardless of etiology, that will be ameliorated by the long-term delivery of a therapeutic protein. Gene therapy can, therefore, be thought of as an in vivo protein production and delivery system, and almost all diseases that are currently treated by the administration of proteins (as well as several diseases for which no treatment is currently available), are candidates for treatment using gene therapy, The field can be divided into two areas: germ cell and somatic cell gene therapy. Germ cell gene therapy refers to the modification of sperm cells, egg cells, zygotes or early stage embryos. On the basis of both ethical and practical criteria, germ cell gene therapy is inappropriate for human use. From an ethical perspective, modifying the germ line would change not only the patient, but also the patient's offspring and, to a small but significant extent, the human gene pool as a whole.

In contrast to germ cell gene therapy, somatic cell gene therapy would affect only the person under treatment (somatic cells are cells that are not capable of developing into whole individuals and include all of the body's cells with the exception of the germ cells). As such, somatic cell gene therapy is a reasonable approach to the treatment and cure of certain disorders in human beings. In a somatic cell gene therapy system, somatic cells (i.e., fibroblasts, hepatocytes or endothelial cells) are removed from the patient, the cells are cultured in vitro, the gene(s) of therapeutic interest are added to the cells and the genetically-engineered cells are characterized and reintroduced into the patient. The means by which these five steps are carried out are the distinguishing features of a given gene therapy system.

To provide an overview of how somatic cell gene therapy might be applied in practice, an example concerning the treatment of hemophilia B will be considered. Hemophilia B is a bleeding disorder that is caused by a deficiency in Factor IX, a protein normally found in the blood. As a candidate for a gene therapy cure, an affected patient would have an appropriate tissue removed (i.e., bone marrow biopsy to recover hematopoietic stem cells, phlebotomy to obtain peripheral leukocytes, a liver biopsy to obtain hepatocytes or a punch biopsy to obtain fibroblasts or keratinocytes). The patient's cells would be isolated, genetically engineered to contain an additional Factor IX gene that directs production of the missing Factor IX and reintroduced into the patient. The patient is now capable of producing his or her own Factor IX and is no longer a Hemophiliac. The physician will most likely. schedule close follow up in the weeks and months after the treatment, but in a literal sense, the patient would have been cured.

In state-of-the-art somatic cell gene therapy systems, it is not possible to direct or target the additional therapeutic DNA to a preselected site in the genome. In fact, in retrovirus-mediated gene therapy, the most widely utilized experimental system retroviruses integrate randomly into independent chromosomal sites in millions to billions of cells. This mixture of infected cells is problematic in two senses: first, since integration site plays a role in the function of the therapeutic DNA, each cell has a different level of function and, second, since the integration of DNA into the genome can trigger undesired events such as the generation of tumorigenic cells, the likelihood of such events is dramatically increased when millions to billions of independent integrations occur.

The problems of populations consisting of large numbers of independent integrants might be avoided in two ways. First, a single cell with a random integration site could be propagated until sufficient numbers of the cloned cell could be introduced into the individual. The cells that make up this clonal population would all function identically. In addition, only a single integration site would be present in the clonal population, significantly reducing the possibility of a deleterious event. Second, a single cell or a population of cells could be treated with therapeutic DNA such that the DNA sequences integrate into a preselected site in the genome. In this case, all the cells would be engineered identically and function identically. Furthermore, the risk of a deleterious integration event would be eliminated. Both the above solutions are demonstrated in this application.

The application of targeting to somatic cell gene therapy has several other advantages in addition to simply introducing additional genes or functional DNA sequences into a cell. In targeted gene therapy, it would be possible to repair, alter, replace or delete DNA sequences within the cell. In the illustration of somatic cell gene therapy discussed above, for example, targeting would allow the patient's non-functional Factor IX gene to be repaired. The ability to repair, alter, replace and delete DNA sequences utilizing targeting technology would expand the range of diseases suitable for treatment-using gene therapy (and for the in vitro production of recombinant proteins as well). As the above discussion suggests, it would be extremely useful to be able to target primary and secondary vertebrate cells.,

SUMMARY OF THE INVENTION

The present invention relates to a method of gene or DNA targeting in cells of vertebrate, particularly mammalian, origin. That is, it relates to a method of introducing DNA into primary or secondary cells of vertebrate origin through homologous recombination or targeting of the DNA, which is introduced into genomic DNA of the primary or secondary cells at a preselected site. The preselected site determines the targeting sequences used. The present invention further relates to homologously recombinant primary or secondary cells, referred to as homologously recombinant (HR) primary or secondary cells, produced by the present method and to uses of the HR primary or secondary cells. The present invention also relates to a method of turning on a gene present in primary cells, secondary cells or immortalized cells of vertebrate origin, which is normally not expressed in the cells or is not expressed at significant levels in the cells. Homologous recombination or targeting is used to replace the regulatory region normally associated with the gene with a regulatory sequence which causes the gene to be expressed at significant levels in the cell.

As described herein, Applicants have demonstrated gene or DNA targeting in primary and secondary cells of mammalian origin. Prior to the present work, gene targeting had been reported only for immortalized tissue culture cell lines (Mansour, Nature 336:348–352 (1988); Shesely, PNAS 88:4294–4298 (1991); Capecchi, M. R., Trends in Genetics 5:70–76 (1989)). As a result of the work described herein, it is now possible to stably integrate exogenous DNA into genomic DNA of a host or recipient primary or secondary cell. The exogenous DNA either encodes a product, such as a therapeutic protein or RNA, to be expressed in primary or secondary cells or is itself a therapeutic product or other product whose function in primary or secondary cells is desired.

As used herein, the term primary cell includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term secondary cell or cell strain refers to cells at all subsequent steps in culturing. That is, the first time a plated primary cell is removed from the culture substrate and replated (passaged), it is referred to, herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

In the method of the present invention, cells to be transfected with exogenous DNA are combined with a DNA construct comprising the exogenous DNA, targeting DNA sequences and, optionally, DNA encoding one or more selectable markers and the resulting combination is treated in such a manner that the DNA construct enters the cells. This is accomplished by subjecting the combination to electroporation, microinjection, or other method of introducing DNA into vertebrate cells (e.g., calcium phosphate precipitation, modified calcium phosphate precipitation, microprojectile bombardment, fusion methodologies, receptor mediated transfer, or polybrene precipitation). Once in the cell, the exogenous. DNA is integrated into the cell's genomic DNA by homologous recombination between DNA sequences in the DNA construct and DNA sequences in the genomic DNA. The sequences involved in targeting (i.e., those which participate in homologous recombination with genomic sequences) can be part of the exogenous DNA or can be separate from (in addition to) the exogenous DNA. The result is homologously recombinant (HR) primary or secondary cells in which the exogenous DNA, as well as other DNA sequences present in the DNA construct, are stably integrated into genomic DNA.

The present method of targeting exogenous DNA has a wide variety of applications. These applications fall into three general types or categories: 1) addition of DNA to sequences already present in vertebrate cells; 2) replacement of DNA sequences present in vertebrate cells; and 3) deletion of sequences normally present in vertebrate cells. For example, the present method can be used to modify primary or secondary cells in order to repair, alter, delete or replace a resident (host cell) gene; to introduce a gene encoding a therapeutic or other product not expressed at significant levels in the primary or secondary cells as obtained; to introduce regulatory sequences into primary or secondary cells; to repair, alter, delete or replace regulatory sequences present in primary or secondary cells; to knock out (inactivate) or remove an entire gene or a gene portion; to produce universal donor cells (e.g., by knocking out cell surface antigens), and to augment production of a gene product already made in the HR primary or secondary cell.

The present method is particularly useful for producing homologously recombinant cells to be used for in vivo protein production and delivery, as described in commonly owned U.S. patent application entitled "In Vivo Protein Production and Deliyvery System for Gene Therapy" (Attorney's Docket No. TKT91-01), filed of even date herewith. The teachings of the patent application entitled "In Vivo Protein Production and Delivery System for Gene Therapy" are incorporated herein by reference.

The present method of targeting is particularly useful to turn on a gene which is present in a cell (primary, secondary or immortalized) but is not expressed in or is not expressed at significant levels in the cells as obtained. The present method can be used for protein production in vitro or for gene, therapy. For example, it can be used to turn on genes, such as the human erythropoietin, growth hormone and insulin genes and other genes (e.g., genes encoding Factor VIII, Factor IX, erythropoietin, alpha-1 antitrypsin, calcitonin, glucocerebrosidase, growth hormone, low density lipoprotein (LDL) receptor, IL-2 receptor and its antagonists, insulin, globin, immunoglobulins, catalytic antibodies, the interleukins, insulin-like growth factors, superoxide dismutase, immune response modifiers, parathyroid hormone, interferons, nerve growth factors, tissue plasminogen activators, and colony stimulating factors) in a cell of any type (primary, secondary or immortalized). In this embodiment, a gene's existing regulatory region can be replaced with a regulatory sequence (from a different-gene or a novel regulatory sequence made by genetic engineering techniques) whose presence in the cell results in expression of the gene. Such regulatory sequences may be comprised of promoters, enhancers, Scaffold-attachment regions, negative regulatory elements, transcriptional initiation sites, regulatory protein binding sites or combinations of these sequences. As a result, an endogenous copy of a gene encoding a desired gene product is turned on (expressed) and an exogenous copy of the gene need not be introduced.

DETAILED DESCRIPTION OF THE INVENTION

Figure 1:
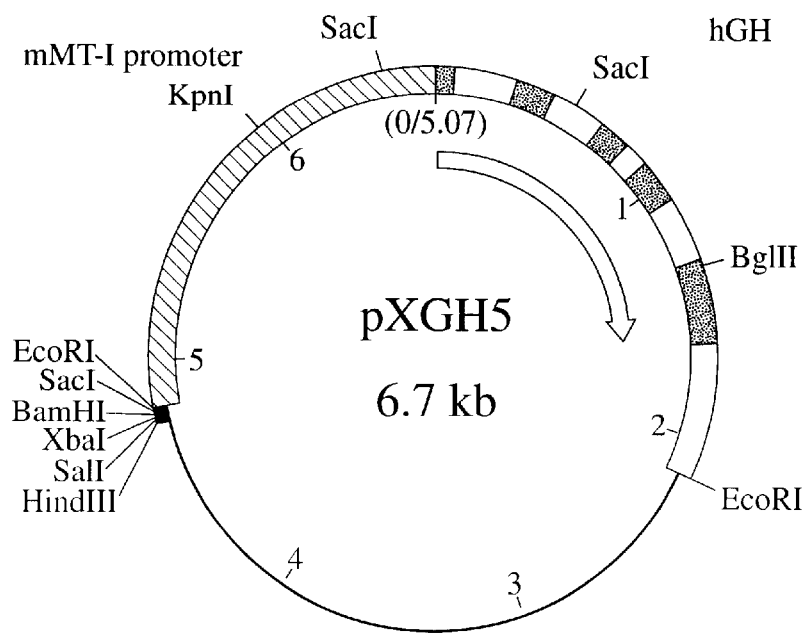
FIG. 1 is a schematic representation of plasmid pXGH5, which includes the human growth hormone (hGH) gene under the control of the mouse metallothionein promoter.

As described herein, Applicants have demonstrated that DNA can be introduced into primary or secondary vertebrate cells in a DNA construct or plasmid and integrated into the genome of the transfected primary or secondary cells by homologous recombination. That is, they have demonstrated gene targeting in primary and secondary mammalian cells. They have further demonstrated that the exogenous DNA has the desired function in the homologously recombinant (HR) cells and that correctly targeted cells can be identified on the basis of a detectable phenotype conferred by a selectable marker gene.

Applicants describe (Example 1) construction of plasmids containing a selectable marker gene (plasmid pcDNEO), a gene encoding a therapeutic product (plasmid pXGH5) or both (pXGH301). They also describe construction of a plasmid useful for targeting to a particular locus (the HPRT locus) in the human genome and selection based upon a drug resistant phenotype (Example 2). This plasmid is designated pE3NEO and its integration into the cellular genomes at the HPRT locus produces cells which have an hprt⁻, 6-TG resistant phenotype and are also G418 resistant. As described, they have shown that pE3NEO functions properly in gene targeting in an established human fibroblast cell line (Example 3), by demonstrating localization of the DNA introduced into established cells within exon 3 of the HPRT gene.

In addition, Applicants demonstrate gene targeting in primary and secondary human skin fibroblasts using pE3Neo (Example 4) and describe construction of a plasmid for targeted insertion of a gene encoding a therapeutic product (human growth hormone [hGH]) into the human genome (Example 5). The subject application further teaches modification of DNA termini to enhance targeting of DNA into genomic DNA (Example 6) and construction of a variety of targeting plasmids. For instance, Applicants describe targeting plasmids for placing a human gene under the control of a murine promoter known to function in human cells (Examples 7 and 10); for targeting to sequences flanking a gene and isolation of targeted secondary fibroblasts using a variety of screening and selection approaches (Examples 8, 9, 11 and 12); for placing a human gene not normally expressed in the primary or secondary cells under the control of a promoter of nonhuman or human origin, to produce HR primary or secondary cells which express the encoded product (Examples 7–12).

Using the methods and DNA constructs or plasmids taught herein or modifications thereof which are apparent to one of ordinary skill in the art, exogenous DNA which encodes a therapeutic product (e.g., protein, ribozyme, nucleic acid) can be inserted at preselected sites in the genome of vertebrate (e.g., mammalian, both human and nonhuman) primary or secondary cells.

The methods and DNA constructs described can be used for a wide variety of purposes. The method can be used to alter primary or secondary cells of vertebrate origin in order to repair, alter, delete or replace DNA already present in the recipient primary or secondary cell; to introduce into primary or secondary cells a gene or DNA sequence (at a preselected site) which encodes a therapeutic product or other desired product or is itself a therapeutic or other product; to add to or replace regulatory sequences present in the primary or secondary cell recipients; to knock out or remove an entire gene or gene portion present in primary or secondary cells; and to produce universal donor cells.

Transfected Cells

Primary and secondary cells to be transfected by the present method can be obtained from a variety of tissues and include all cell types which can be maintained in culture. For example, primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, hepatocytes and precursors of these somatic cell types. Primary cells are preferably obtained from the individual to whom the transfected primary or secondary cells are administered. However, primary cells may be obtained from a donor (other than the recipient) of the same species or another species (e.g., nonhuman primates, mouse, rat, rabbit, cat, dog, pig, cow, bird, sheep, goat, horse).

Transfected primary and secondary cells have been produced, with or without phenotypic selection, as described in co-pending application entitled "In Vivo Protein Production and Delivery System for Gene Therapy". (Attorney's Docket No. TKT91-01), filed of even date herewith and shown to express exogenous DNA encoding a therapeutic product.

Exogenous DNA

Exogenous DNA incorporated into primary or secondary cells by the present method is: 1) DNA which encodes a translation or transcription product whose expression in primary or secondary cells is desired, such as a product useful to treat an existing condition or prevent it from occurring and 2) DNA which does not encode a gene product but is itself useful, such as in treating an existing condition or preventing it from occurring.

DNA incorporated into primary or secondary cells can be an entire gene encoding an entire desired product or a gene portion which encodes, for example, the active or functional portion(s) of the product. The product can be, for example, a hormone, a cytokine, an antigen, an antibody, an enzyme, a clotting factor, a transport protein, a receptor, a regulatory protein, a structural protein, an anti-sense RNA, a ribozyme or a protein or a nucleic acid which does not occur in nature (i.e., a novel protein or novel nucleic-acid). The DNA can be obtained from a source in which it occurs in nature or can be produced, using genetic engineering techniques or synthetic processes. The DNA transfected into primary or secondary cells can encode one or more therapeutic products. After transfection into primary or secondary cells, the exogenous DNA is stably incorporated into the recipient cell's genome (along with the additional sequences present in the DNA construct used), from which it is expressed or otherwise functions.

Selectable Markers

A variety of selectable markers can be incorporated into primary or secondary cells. For example, a selectable marker which confers a selectable phenotype such as drug resistance, nutritional auxotrophy, resistance to a cytotoxic agent or expression of a surface protein, can be used.

Selectable marker genes which can be used include neo, gpt, dhfr, ada, pac, hyg, mdrl and hisD. The selectable phenotype conferred makes it possible to identify and isolate recipient primary or secondary cells. Selectable markers can be divided into two categories: positive selectable and negative selectable. In positive selection, cells expressing the positive selectable marker are capable of surviving treatment with a selective agent (such as neo, gpt, dhfr, ada, pac, hyg, mdrl and hisD). In negative selection, cells expressing the negative selectable marker are destroyed in the presence of the selective agent (e.g., tk, gpt).

DNA Constructs

DNA constructs, which include exogenous DNA encoding a desired product, targeting sequences for homologous recombination and, optionally, DNA encoding one or more selectable markers are used to transfect primary or secondary cells in which homologous recombination is to occur. In this embodiment, DNA sequences necessary for expression of the exogenous DNA will generally be present as well. DNA constructs which include exogenous DNA sequences which do not encode a gene product (and are the desired product) and, optionally, include DNA encoding a selectable marker, can also be used to transfect primary and secondary cells.

The exogenous DNA, targeting sequences and selectable marker can be introduced into cells on a single DNA construct or on separate constructs. The total length of the DNA construct will vary according to the number of components (exogenous DNA, targeting sequences, selectable marker gene) and the length of each. The entire construct length will generally be at least 20 nucleotides. In a construct in which the exogenous DNA has sufficient homology with genomic DNA to undergo homologous recombination, the construct will include a single component, the exogenous DNA. In this embodiment, the exogenous DNA, because of its homology, serves also to target integration into genomic DNA and additional targeting sequences are unnecessary. Such a construct is useful to knock out, replace or repair a resident DNA sequence, such as an entire gene, a gene portion, a regulatory element or portion thereof or regions of DNA which, when removed, place regulatory and structural sequences in functional proximity. It is also useful when the exogenous DNA is a selectable marker.

In another embodiment, the DNA construct includes exogenous DNA and one or more separate targeting sequences, generally located at both ends of the exogenous DNA sequence. Targeting sequences are DNA sequences normally present in the primary or secondary cell genome in the genome of the cells as obtained [e.g., an essential gene, a nonessential gene or noncoding DNA, or present in the genome through a previous modification] Such a construct is useful to integrate exogenous DNA encoding a therapeutic product, such as a hormone, a cytokine, an antigen, an antibody, an enzyme, a clotting factor, a transport protein, a receptor, a regulatory protein, a structural protein, an antisense RNA, a ribozyme or a protein or a nucleic acid which does not occur in nature. In particular, exogenous DNA can encode one of the following: Factor VIII, Factor IX, erythropoietin, alpha-1 antitrypsin, calcitonin, glucocerebrosidase, growth hormone, low density lipoprotein (LDL) receptor, IL-2 receptor and its antagonists, insulin, globin, immunoglobulins, catalytic antibodies, the interleukins, insulin-like growth factors, superoxide dismutase, immune responder modifiers, parathyroid hormone, interferons, nerve growth factors, tissue plasminogen activators, and colony stimulating factors. Such a construct is also useful to integrate exogenous DNA which is a therapeutic product, such as DNA sequences sufficient for sequestration of a protein or nucleic acid in the transfected primary or secondary cell, DNA sequences which bind to a cellular regulatory protein, DNA sequences which alter the secondary or tertiary chromosomal structure and DNA sequences which are transcriptional regulatory elements into genomic DNA of primary or secondary cells.

In a third embodiment, the DNA construct includes exogenous DNA, targeting DNA sequences and DNA encoding at least one selectable marker. In this third embodiment, the order of construct components can be: targeting sequences-exogenous DNA-DNA encoding a selectable marker(s)-targeting sequences. In this embodiment, one or more selectable markers are included in the construct, which makes selection based on a selectable phenotype possible. Cells that stably integrate the construct will survive treatment with the selective agent; a subset of the stably transfected cells will be HR cells, which can be identified by a variety of techniques, including PCR, Southern hybridization and phenotypic screening.

In a fourth embodiment, the order of components in the DNA construct can be: targeting sequence-selectable marker 1—targeting sequence—selectable marker 2. In this embodiment selectable marker 2 displays the property negative selection, that is, the gene product of selectable marker 2 can be selected against by growth in an appropriate media formulation containing an agent (typically a drug or metabolite analog) which kills cells expressing selectable marker 2. Recombination between the targeting sequences flanking selectable marker 1 with homologous sequences in the host cell genome results in the targeted integration of selectable marker 1, while selectable marker 2 is not integrated. Such recombination events generate cells which are stably transfected with selectable marker 1 but not stably transfected with selectable marker 2, and such cells can be selected for by growth in the media containing the selective agent which selects for selectable marker 1 and the selective agent which selects against selectable marker 2.

In all embodiments of the DNA construct, exogenous DNA can encode one or more products, can be one or more therapeutic products or one or more of each, thus making it possible to deliver multiple products.

Replacement of a Regulatory Sequence of a Gene by Homologous Recombination

As taught herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, Scaffold-attachment regions, negative regulatory elements, transcriptional initiation sites, reguatory protein binding sites or combinations of said sequences. (Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules).

Several embodiments are possible. First, the targeting event may be a simple insertion of the regulatory sequence, placing the gene under the control of the new regulatory sequence (for example, inserting a new promoter or enhancer or both upstream of a gene). Second, the targeting event may be a simple deletion of a regulatory element, such as the deletion of a tissue-specific negative regulatory element. Third, the targeting event may replace an existing element; for example, a tissue-specific enhancer can be replaced by an enhancer that has broader or different cell-type specificity than the naturally-occurring elements. In this embodiment the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the-property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyltransferase (gpt) gene.

Transfection of Primary or Secondary Cells and Production of Clonal or Heterogenous Cell Strains The method of the present invention is carried out as follows: Vertebrate tissue is first obtained; this is carried out using known procedures, such as punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

Figure 2:
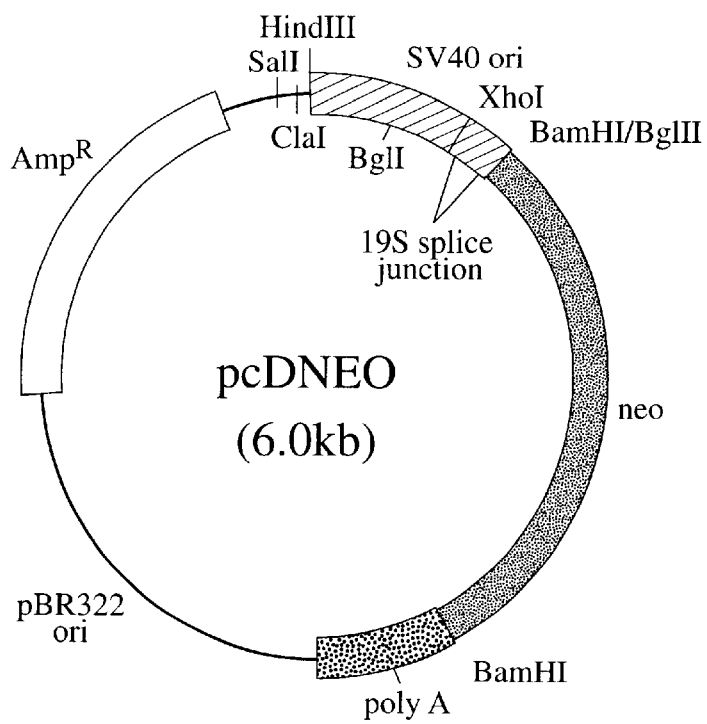
FIG. 2 is a schematic representation of plasmid pcDNEO, which includes the neo coding region (BamHI-BglII fragment) from plasmid pSV2neo inserted into the BamHI site of plasmid pcD; the Amp-R and pBR322ori sequences from pBR322; and the polyA, 16S splice junctions and early promoter regions from sv40.

The resulting primary cell mixture can be transfected directly or it can be cultured first, removed from the culture plate and resuspended before transfection is carried out. Primary cells or secondary cells are combined with exogenous DNA to be stably integrated into their genomes and, optionally, DNA encoding a selectable marker, and treated in order to accomplish transfection. The exogenous DNA and selectable marker-encoding DNA are each on a separate construct (e.g., pXGH5 and pcDNEO, see FIGS. 1 and 2) or on a single construct (e.g., pXGH301, see FIG. 3) and an appropriate quantity of DNA to ensure that at least one stably transfected cell containing and appropriately expressing exogenous DNA is produced. In general, 0.1 to $^{500}$ μg DNA is used.

Using the present methods to introduce only a selectable marker gene, between 170 (1 in 588 starting cells treated by electroporation) and 2000 (1 in 49 starting cells treated by microinjection) stably transfected cells are generated per 100,000 starting cells. Using the present methods to introduce a therapeutic gene as well as a selectable marker gene, between 7 (1 in 14,705 starting cells treated by electroporation) and 950 (1 in 105 starting cells treated by microinjection) stably transfected cells are generated per 100,000 starting cell. Of these stable transfectants, from 43 to 90% express the gene of therapeutic interest. Since only a single appropriately expressing cell is required, it is clearly possible to use substantially fewer starting cells. Conversely, using transfection techniques which are substantially less efficient than the present methods, it would not be possible to obtain even a single such cell unless large amount of the individual's tissue is used as the source of starting cells.

In one embodiment of the present method of producing transfected primary or secondary cells, transfection is effected by electroporation, as described in Example 1. Electroporation is carried out at appropriate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. As described herein, electroporation is very efficient if carried out at an electroporation voltage in the range of 250–300 volts and a capacitance of 960 μFarads (see Example 1). Total DNA of approximately 0.1 to 500 μg is generally used. Total DNA of 60 μg and voltage of 250–300 volts with capacitance of 960 μFarads for a time constant 14–20 of msec. has been used and shown to be efficient.

In another embodiment of the present method, primary or secondary cells are transfected using microinjection. Alternatively, known methods such as calcium phosphate precipitation, modified calcium phosphate precipitation and polybrene precipitation, liposome fusion and receptor-mediated gene delivery can be used to transfect cells. A stably transfected cell is isolated and cultured and subcultivated, under culturing conditions and for sufficient time, to propagate the stably transfected secondary cells and produce a clonal cell strain of transfected secondary cells. Alternatively, more than one transfected cell is cultured and subcultured, resulting in production of a heterogenous cell strain.

Transfected primary or secondary cells undergo a sufficient number of doublings to produce either a clonal cell strain or a heterogenous cell strain of sufficient size to provide the therapeutic product to an individual in effective amounts. In general, for example, 0.1 $cm^2$ of skin is biopsied and assumed to contain 100,000 cells; one cell is used to produce a clonal cell strain and undergoes approximately 27 doublings to produce 100 million transfected secondary cells. If a heterogenous cell strain is to be produced from an original transfected population of approximately 100,000 cells, only 10 doublings are needed to produce 100 million transfected cells.

The number of required cells in a transfected clonal or heterogenous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. To put these factors in perspective, to deliver therapeutic levels of human growth hormone in an otherwise healthy 10 kg patient with isolated growth hormone deficiency, approximately one to five hundred million transfected fibroblasts would be necessary (the volume of these cells is about that of the very tip of the patient's thumb).

Implantation of Clonal Cell Strains or Heterogenous Cell Strains of Transfected Secondary Cells The homologously recombinant cells produced as described above are introduced into an individual to whom the therapeutic product is to be delivered, using known methods. The clonal cell strain or heterogenous cell strain is introduced into an individual, using known methods, using various routes of administration and at various sites (e.g., renal subcapsular, subcutaneous, central nervous system (including intrathecal), intravascular, intrahepatic, intrasplanchnic, intraperitoneal (including intraomental), or intramuscular implantation). Once implanted in the individual, the transfected cells produce the therapeutic product encoded by the exogenous DNA or are affected by the exogenous DNA itself. For example, an individual who has been diagnosed with Hemophilia B, a bleeding disorder that is caused by a deficiency in Factor IX, a protein normally found in the blood, is a candidate for a gene therapy cure. The patient has a small skin biopsy performed; this is a simple procedure which can be performed on an out-patient basis. The piece of skin, approximately the size of a matchhead, is taken, for example, from under the arm and requires about one minute to remove. The sample is processed, resulting in isolation of the patient's cells (in this case, fibroblasts) and genetically engineered to produce the missing Factor IX. Based on the age, weight, and clinical condition of the patient, the required number of cells are grown in large-scale culture. The entire process usually requires 4–6 weeks and, at the end of that time, the appropriate number of genetically-engineered cells are introduced into the individual, once again as an out-patient (e.g., by injecting them back under the patient's skin). The patient is now capable of producing his or her own Factor IX and is no longer a hemophiliac.

As this example suggests, the cells used will generally be patient-specific genetically-engineered cells. It is possible, however, to obtain cells from another individual of the same species or from a different species. Use of such cells might require administration of an immunosuppressant, alteration of histocompatibility antigens, or use of a barrier device to prevent rejection of the implanted cells. For many diseases, this will be a one-time treatment and, for others, multiple gene therapy treatments will be required.

Uses of Homologously Recombinant Primary and Secondary Cells and Cell Strains

HR primary or secondary cells or cell strains have wide applicability as a vehicle or delivery system for therapeutic products, such as enzymes, hormones, cytokines, antigens, antibodies, clotting factors, anti-sense RNA, regulatory proteins, transcription proteins, receptors, structural proteins, ribozymes, novel (non-naturally occurring) proteins and nucleic acid products, and engineered DNA. For example, transfected primary or secondary cells can be used to supply a therapeutic protein, including, but not limited to, Factor VIII, Factor IX, erythropoietin, alpha-1 antitrypsin, calcitonin, glucocerebrosidase, growth hormone, low density lipoprotein (LDL) receptor, IL-2 receptor and its antagonists, insulin, globin, immunoglobulins, catalytic antibodies, the interleukins, insulin-like growth factors, superoxide dismutase, immune responder modifiers, parathyroid hormone, interferons, nerve growth factors, tissue plasminogen activators, and. colony stimulating factors. Alternatively, transfected primary and secondary cells can be used to immunize an individual (i.e., as a vaccine). In the case where targeting is utilized to introduce additional DNA sequences into the genome, the ability to pre-select the integration site offers many advantages as compared to random integration. For example, the additional sequences can be directed to a region of the genome that allows appropriate expression and to regions that are distant from oncogenes. The sequences can be targeted to non-essential or essential genes or to non-coding sequences as desired. The choice of site can be determined based on the above considerations or based on known integration sites of well-characterized, appropriately-functioning transfected cells.

The wide variety of uses of cell strains of the present invention can perhaps most conveniently be summarized as shown below. The cell strains can be used to deliver the following therapeutic products.

1. a secreted protein with predominantly systemic effects;
2. a secreted protein with predominantly local effects;
3. a membrane protein imparting new or enhanced cellular responsiveness;
4. membrane protein facilitating removal of a toxic product;
5. a membrane protein marking or targeting a cell;
6. an intracellular protein;
7. an intracellular protein directly affecting gene expression;
8. an intracellular protein with autolytic effects;
9. gene product-engineered DNA which binds to or sequesters a regulatory protein;
10. a ribozyme; and
11. antisense-engineered RNA to inhibit gene expression.

The transfected primary or secondary cells of the present invention can be used to administer therapeutic proteins (e.g., hormones, enzymes, clotting factors) which are presently administered intravenously, intramuscularly or subcutaneously, which requires patient cooperation and, often, medical staff participation. When transfected primary or secondary cells are used, there is no need for extensive purification of the polypeptide before it is administered to an individual, as is generally necessary with an isolated polypeptide. In addition, transfected primary or secondary cells of the present invention produce-the therapeutic product as it would normally be produced.

An advantage to the use of transfected primary or secondary cells of the present invention is that by controlling the number of cells introduced into an individual, one can control the amount of the product delivered to the body. In addition, in some cases, it is possible to remove the transfected cells if there is no longer a need for the product. A further advantage of treatment by use of transfected primary or secondary cells of the present invention is that production of the therapeutic product can be regulated, such as through the administration of zinc, steroids or an agent which affects translation or transcription of a protein product or nucleic acid product or affects the stability of a nucleic acid product.

The subject invention will now be illustrated by the following examples, which are not intended to be limiting in any way.

EXAMPLES

Example 1

Stable Transfection of Primary or Secondary Human cells

Figure 3:
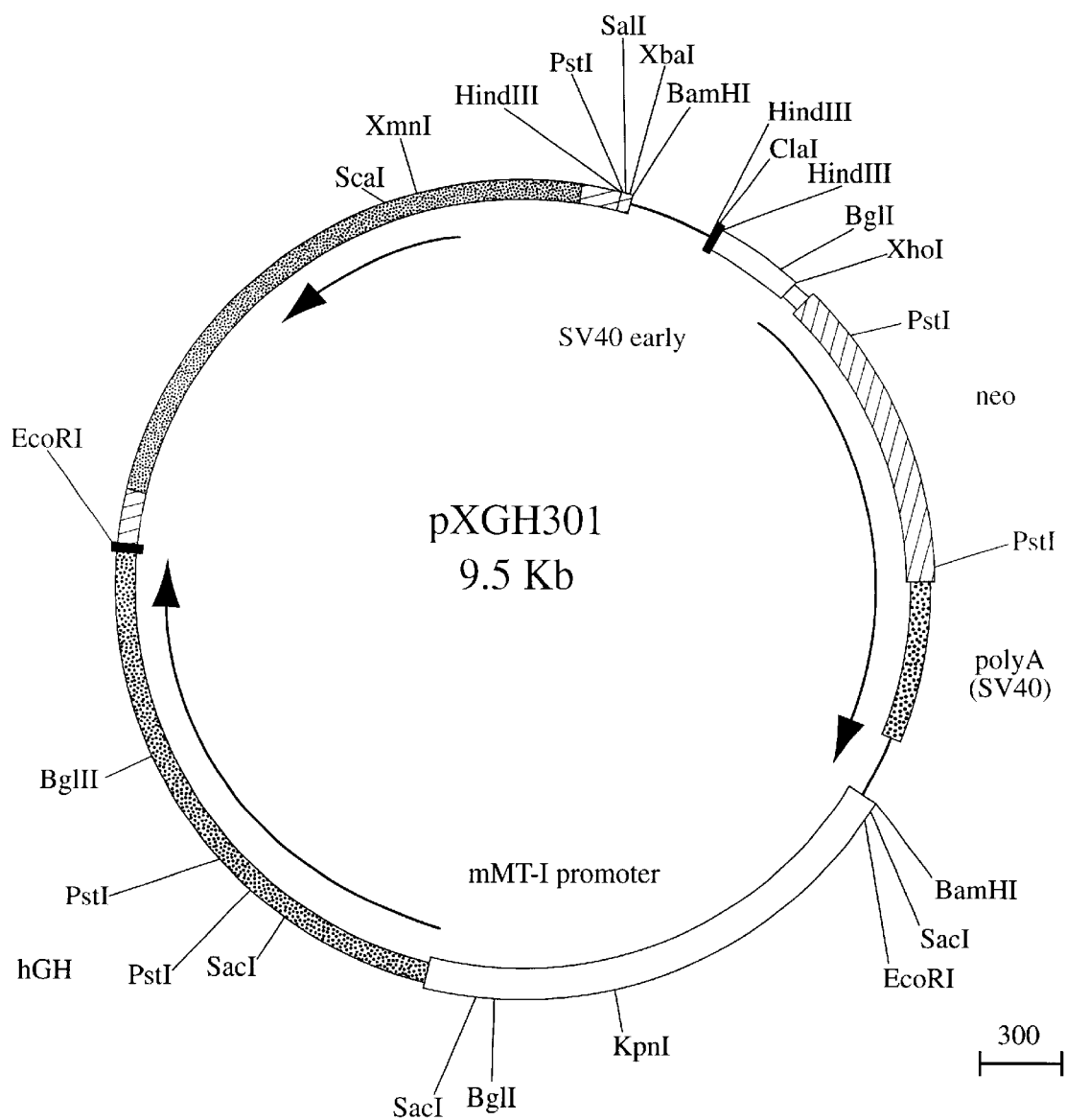
FIG. 3 is a schematic representation of plasmid pXGH301 which includes the human growth hormone gene and the neo gene.

1. Generation of a Construct IXGH301) Containing Both the Human Growth Hormone and Neomycin Resistance Genes pXGH301 was constructed by a two-step procedure. The SaII-ClaI fragment from pBR322 (positions 23-651 in pBR322) was isolated and inserted into SaII-ClaI digested pcDNEO, introducing a BamHI site upstream of the SV40 early promoter region of pcDNEO. This plasmid, pBNEO was digested with BamHI, and the 2.1 kb fragment containing the neo gene under the control of the SV40 early promoter, was isolated and inserted into BamHI digested pXGH5. A plasmid with a single insertion of the 2.1 kb BamHI fragment was isolated in which neo and hGH are transcribed in the same direction relative to each other. This plasmid was designated pXGH301 (FIG. 3).

2. Stable Transfection of Primary or Secondary Human Cells

Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na$_2$HPO$_4$, 6 mM dextrose). The cells are recentrifuged, the supernatant aspirated, and the cells resuspended in electroporation buffer containing 1 mg/ml acetylated bovine serum albumin. The final cell suspension contains approximately 3×10$^6$ cells/ml. Electroporation should be performed immediately following resuspension.

Supercoiled plasmid DNA is added to a sterile cuvette with a 0.4 cm electrode gap (Bio-Rad). The final DNA concentration is generally at least 120 μg/ml. 0.5 ml of the cell suspension (containing approximately 1.5×10$^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 msec should be observed.

Electroporated cells are maintained at room temperature for approximately 5 min, and the contents of the cuvette are then gently removed with a sterile transfer pipette. The cells are added directly to 10 ml of prewarmed nutrient media (as above with 15% calf serum) in a 10 cm dish and incubated as described above. The following day, the media is aspirated and replaced with 10 ml of fresh media and incubated for a further 16–24 hrs. Subculture of cells to determine cloning efficiency and to select for G418-resistant colonies is performed the following day. Cells are trypsinized, counted and plated; typically, fibroblasts are plated at 10$^3$ cells/10 cm dish for the determination of cloning efficiency and at 1–2×10$^4$ cells/10 cm dish for: G418 selection.

Human fibroblasts are selected for G418 resistance in medium consisting of 300–400 μg/ml G418 (Geneticin, disulfate salt with a potency of approximately 50%; Gibco) in fibroblasts nutrient media (with 15% calf serum). Cloning efficiency is determined in the absence of G418. The plated cells are incubated for 12–14 days, at which time colonies are fixed with formalin, stained with crystal violet and counted (for cloning efficiency plates) or isolated using cloning cylinders (for G418 plates) Electroporation and selection of rabbit fibroblasts is performed essentially as described for human fibroblasts, with the exception of the selection conditions used. Rabbit fibroblasts are selected for G418 resistance in medium containing 1 gm/ml G418.

Fibroblasts were isolated from freshly excised human foreskins. Cultures were seeded at 50,000 cells/cm$^2$ in DMEM+10% calf serum. When cultures became confluent fibroblasts were harvested by trypsinization and transfected by electroporation. Electroporation conditions were evaluated by transfection with the plasmid pcDNEO. A representative electroporation experiment using near optimal conditions (60 μg of plasmid pcDNE0 at an electroporation voltage of 250 volts and a capacitance setting of 960 μFarads) resulted in one G418$^r$ coloney per 588. treated cells (0.17% of all cells treated), or one G418$^r$ colony per 71 clonable cells (1.4%).

When nine separate electroporation experiments at near optimal conditions (60 μg of plasmid pcDneo at an electroporation voltage of 300 volts and a capacitance setting of 960 μFarads) were performed, an average of one G418$^r$ colony per 1,899 treated cells (0.05%) was observed, with a range of 1/882 to 1/7,500 treated cells. This corresponds to an average of one G418$^r$ colony per 38 clonable cells (2.6%).

Low passage primary human fibroblasts were converted to hGH expressing cells by co-transfection with plasmids pcDNEO and pXGH5. Typically, 60 μg of an equimolar mixture of the two plasmids were transfected at near optimal conditions (electroporation voltage of 300 volts and a capacitance setting of 960 μFarads). The results of such an experiment resulted in one G418$^r$ colony per 14,705 treated cells.

hGH expression data for these and other cells isolated under identical transfection conditions are summarized below. Ultimately, 98% of all G418$^r$ colonies could be expanded to generate mass cultures.

| | |
|---|---|
| Number of G418$^r$ Clones Analyzed | 154 |
| Number of G418$^r$/hGH Expressing Clones | 65 |
| Average hGH Expression Level | 2.3 μg hGH/10$^6$ Cells/24 hr |
| Maximum hGH Expression Level | 23.0 μg hGH/10$^6$ Cells/24 hr |

Example 2

Generation of a Construct Useful for Selection of Gene Targeting Events in Human Cells One approach to selecting the targeted events is by genetic selection for the loss of a gene function due to the integration of transfecting DNA. The human HPRT locus encodes the enzyme hypoxanthine-phosphoribosyl transferase. hprt$^{31}$ cells can be selected for by growth in medium containing the nucleoside analog 6-thioguanine (6-TG): cells with the wild-type (HPRT+) allele are killed by 6-TG, while cells with mutant (hprt$^-$) alleles can survive. Cells harboring targeted events which disrupt HPRT gene function are therefore selectable in 6-TG medium.

To construct a plasmid for targeting to the HPRT locus, the 6.9 kb HindIII fragment extending from positions 11,960–18,869 in the HPRT sequence (Genebank name HUMHPRTB; Edwards, A. et al., Genomics 6:593–608 (1990)) and including exons 2 and 3 of the HPRT gene, is subcloned into the HindIII site of pUC12. The resulting clone is cleaved at the unique, XhoI site in exon 3 of the HPRT gene fragment and the 1.1 kb SalI-XhoI fragment containing the neo gene from pMC1Neo (Stratagene) is inserted, disrupting the coding sequence of exon 3. One orientation, with the direction of neo transcription opposite that of HPRT transcription was chosen and designated pE3Neo. The replacement of the normal HPRT exon 3 with the neo-disrupted version will result in an hprt$^-$, 6-TG resistant phenotype. Such cells will also be G418 resistant.

Example 3

Gene Targeting in an Established Human Fibroblast Cell Line

Gene targeting has previously only been reported for immortalized tissue culture cell lines. As a positive control for targeting and to establish that pE3Neo functions properly in gene targeting, the human fibrosarcoma cell line HT1080 (ATCC CCL 121) was transfected with pE3Neo by electroporation.

HT1080 cells were maintained in HAT (hypoxanthine/aminopterin/xanthine) supplemented DMEM with 15% calf serum (Hyclone) prior to electroporation. Two days before electroporation, the cells are switched to the same medium without aminopterin. Exponentially growing cells were trypsinized and diluted in DMEM/15% calf serum, centrifuged, and resuspended in PBS (phosphate buffered saline) at a final cell bolume of 13.3 million cells per ml. pE3Neo is digested with HindIII, separating the 8 kb HPRT-neo fragment from the pUC12 backbone, purified by phenol extraction and ethanol precipitation, and resuspended at a concentration of 600 µg/ml. 50 µl (30 µg) was added to the electroporation cuvette (0.4 cm electrode gap; Bio-Rad Laboratories), along with 750 µl of the cell suspension (10 million cells). Electroporation was at 450 volts, 250 µFarads (Bio-Rad Gene Pulser; Bio-Rad Laboratories). The contents of the cuvette were immediately added to DMEM with 15% calf serum to yield a cell suspension of 1 million cells per 25 ml media. 25 ml of the treated cell suspension was plated onto 150 mm diameter tissue culture dishes and incubated at 37° C., 5% $CO_2$. 24 hrs later, a G418 solution was added directly to the plates to yield a final concentration of 800 µg/ml C418. Five days later the media was replaced with DMEM/15% calf serum/800 µg/ml G418. Nine days after electroporation, the media was replaced with DMEM/15% calf serum/800 µg/ml G418 and 10 µM 6-thioguanine. Colonies resistant to G418 and 6-TG were picked using cloning cylinders 14–16 days after the dual selection was initiated.

The results of five representative targeting experiments in HT1080 cells are shown in the table below.

| Transfection | Number of Treated Cells | Number of $G418^r$ $6\text{-}TG^r$ Clones |
|---|---|---|
| 1 | $1 \times 10^7$ | 32 |
| 2 | $1 \times 10^7$ | 28 |
| 3 | $1 \times 10^7$ | 24 |
| 4 | $1 \times 10^7$ | 32 |
| 5 | $1 \times 10^7$ | 66 |

For transfection 5, control plates designed to determine the overall yield of $G418^r$ colonies indicated that 33,700 $G418^r$ colonies could be generated from the initial $1 \times 10^7$ treated cells. Thus, the ratio of targeted to non-targeted events is 66/33,700, or 1 to 510. In the five experiments combined, targeted events arise at a frequency of $3.6 \times 10^{-6}$, or 0.00036% of treated cells.

Restriction enzyme and Southern hybridization experiments using probes derived from the neo and HPRT genes localized the neo gene to the HPRT locus at the predicted site within HPRT exon 3.

Example 4

Gene Targeting in Primary and Secondary Human Skin Fibroblasts pE3Neo is digested with HindIII, separating the 8 kb HPRT-neo fragment from the pUC12 backbone, and purified by phenol extraction-and ethanol precipitation. DNA was resuspended at 2 mg/ml. Three million secondary human foreskin fibroblasts cells in a volume of 0.5 ml were electroporated at 250 volts and 960 pFarads, with 100 µg. of HindIII pE3Neo (50 µl). Three separate transfections were performed, for a total of 9 million treated cells. Cells are processed and selected for G418 resistance as described in Example 1, except that 500,000 cells per 150 mm culture dish are plated for G418 selection. After 10 days under selection, the culture medium is replaced with human fibroblast nutrient medium containing 400 µg/ml G418 and 10 µM 6-TG. Selection with the two drug combination is continued for 10 additional days. Plates are scanned microscopically to localize human fibroblast colonies resistant to both drugs. The fraction of $G418^r$ t-$TG^r$ colonies is 4 per 9 million treated cells. These colonies constitute 0.0001% (or 1 in a million) of all cells capable of forming colonies. Control plates designed to determine the overall yield of $C418^r$ colonies indicated that 2,850 $G418^r$ colonies could be generated from the initial $9 \times 10^6$ treated cells. Thus, the ratio of targeted to non-targeted events is 4/2,850, or 1 to 712. Restriction enzyme and Southern hybridization experiments using probes derived from the neo and HPRT genes were used to localize the neo gene to the HPRT locus at the predicted site within HPRT exon 3 and demonstrate that targeting had occurred in these four clonal cell strains. Colonies resistant to both drugs have also been isolated by transfecting primary cells (1/3. $0 \times 10^7$).

Example 5

Generation of A Construct for Targeted Insertion of A Gene of Therapeutic Interest Into the Human Genome and Its Use in Gene Targeting A variant of pE3Neo, in which a gene of therapeutic interest is inserted within the HPRT coding region, adjacent to or near the neo gene, can be used to target a gene of therapeutic interest to a specific position in a recipient primary or secondary cell genome. Such a variant of pE3Neo can be constructed for targeting the hGH gene to the HPRT locus.

pXGH5 is digested with EcoRI and the 4.1 kb fragment containing the hGH gene and-linked mouse metallothionein (mMT) promoter is isolated. The EcoRI overhangs are filled in with the Klenow fragment from E. coli DNA polymerase. Separately, pE3Neo is digested with XhoI, which cuts at the junction of the neo fragment and HPRT exon 3 (the 3' junction of the insertion into exon 3). The XhoI overhanging ends of the linearized plasmid are filled in with the Klenow fragment from E. coli DNA polymerase, and the resulting fragment is ligated to the 4.1 kb blunt-ended hCH-mMT fragment. Bacterial colonies derived from the ligation mixture are screened by restriction enzyme analysis for a single copy insertion of the hGH-mMT fragment and one orientation, the hGH gene transcribed in the same direction as the neo gene, is chosen and designated pE3Neo/hGH. pE3Neo/hGH is digested with HindIII, releasing the 12.1 kb fragment containing HPRT, neo and mMT-hGH sequences. Digested DNA is treated and transfected into primary or secondary human fibroblasts as described in Example 4. $G418^r$ $TG^r$ colonies are selected and analyzed for targeted insertion of the mMT-hGH and neo sequences into the HPRT gene as described in Example 4. Individual colonies are assayed for hGH expression using a commercially available immunoassay (Nichols Institute).

Example 6

Modification of DNA Termini to Enhance Targeting

Several lines of evidence suggest that 3'-overhanging ends are involved in certain homologous recombination pathways of E. coli, bacteriophage, S. cerevisiae, and Xenopus laevis. In Xenopus laevis oocytes, molecules with 3'-overhanging ends of several hundred base pairs in length underwent recombination with similarly treated molecules much more rapidly after microinjection than molecules with very short overhangs (4 bp) generated by restriction enzyme digestion. In yeast, the generation of 3'-overhanging ends several hundred base pairs in length appears to be a rate limiting step in meiotic recombination. No evidence for an involvement of 3'-overhanging ends in recombination in human cells has been reported, and in no case have modified DNA substrates of any sort been shown to promote targeting (one form of homologous recombination) in any species. In human cells, the effect of 3'-overhanging ends on targeting is untested. The experiment described in the following example suggests that 5'-overhanging ends are most effective for targeting in primary and secondary human fibroblasts.

There have been no reports on the enhancement of targeting by modifying the ends of the transfecting DNA molecules. This example serves to illustrate that modification of the ends of linear DNA molecules, by conversion of the molecules' termini from a doublestranded form to a single-stranded form, can stimulate targeting into the genome of primary and secondary human-fibroblasts.

1100 μg of plasmid pE3Neo (Example 2) is digested with HindIII. This DNA can be used directly after phenol extraction and ethanol precipitation, or the 8 kb HindIII fragment containing only HPRT and the neo gene can be separated away from the pUC12 vector sequences by gel electrophoresis. ExoIII digestion of the HindIII digested DNA results in extensive exonucleolytic digestion at each end, initiating at each free 3' end, and leaving 5'-overhanging ends. The extent of exonucleolytic action and, hence, the length of the resulting 5'-overhangings, can be controlled by varying the time of ExoIII digestion. ExoIII digestion of 100 μg of HindIII digested pE3Neo is carried out according to the supplier's recommended conditions, for times of 30 sec, 1 min, 1.5 min, 2 min, 2.5 min, 3 min, 3.5 min, 4 min, 4.5 min, and 5 min. To monitor the extent of digestion an aliquot from each time point, containing 1 μg of ExoIII treated DNA, is treated with mung bean nuclease (Promega), under conditions recommended by the supplier, and the samples fractionated by gel electrophoresis. The difference in size between non-treated, HindIII digested pE3Neo and the same molecules treated with ExoIII and mung bean nuclease is measured. This size difference divided by two gives the average length of the 5'-overhang at each end of the molecule. Using the time points described above and digestion at 30°, the 5'-overhangs produced should range from 100 to 1,000 bases.

60 μg of ExoIII treated DNA (total HindIII digest of pE3NEO) from each time point is purified and electroporated into primary or secondary human fibroblasts under the conditions described in Example 4. The degree to which targeting is enhanced by each ExoIII treated preparation is quantified by counting the number of G418$^r$6-TG$^r$ colonies and comparing these numbers to targeting with HindIII digested pE3Neo that was not treated with ExoIII.

The effect of 3'-overhanging ends can-also be quantified using an analogous system. In this case HindIII digested pE3Neo is treated with bacteriophage T7 gene 6 exonuclease (United States Biochemicals) for varying time intervals under the supplier's recommended conditions. Determination of the extent of digestion (average length of 3'-overhang produced per end) and electroporation conditions are as described for ExoIII treated DNA. The degree to which targeting is enhanced by each T7 gene 6 exonuclease treated preparation is quantified by counting. The number of G418$^r$6-TG$^r$ colonies and comparing these numbers to targeting with HindIII digested pE3NEO that was not treated with T7 gene 6 exonuclease.

Other methods for generating 5' and 3' overhanging ends are possible, for example, denaturation and annealing of two linear molecules that partially overlap with each other will generate a mixture of molecules, each molecule having 3'-overhangs at both ends or 5'-overhangs at both ends, as well as reannealed fragments indistinguishable from the starting linear molecules. The length of the overhangs is determined by the length of DNA that is not in common between the two DNA fragments.

Example 7

Construction of Targeting Plasmids for Placing the Human Erythropoietin Gene Under the Control of the Mouse Metallothionein Promoter in Primary and Secondary Human Fibroblasts The following serves to illustrate one embodiment of the present invention, in which the normal positive and negative regulatory sequences upstream of the human erythropoietin (EPO) gene are altered to allow expression of human erythropoietin in primary or secondary human fibroblast strains, which do not express EPO in significant quantities as obtained.

A region lying exclusively upstream of the human EPO coding region can be amplified by PCR. Three sets of primers useful for this purpose were designed after analysis of the published human EPO [Genbank designation HUMERPA; Lin, F-K., et al., *Proc. Natl. Acad. Sci, USA*. 82:7580–7584 (1985)]. These primer pairs can amplify fragments of 609, 603, or 590 bp.

| Primer | HUMERPA Coordinate | Sequence | Fragment Size |
|---|---|---|---|
| F1 | 2->20 | 5' AGCTTCTGGGCTTCCAGAC (SEQ ID NO:1) | |
| R1 | 610>595 | 5'GGGGTCCCTCAGCGAC (SEQ ID NO:2) | 609 bp |
| F2 | 8->24 | 5' TGGGCTTCCAGACCCAG (SEQ ID NO:3) | |
| R2 | 601>-595 | 5' GGGGTCCCTCAGCGAC (SEQ ID NO:2) | 603 bp |
| F3 | 21->40 | 5' CCAGCTACTTTGCGGAACTC (SEQ ID NO:4) | |
| R3 | 601->595 | 5' GGGGTCCCTCAGCGAC (SEQ ID NO:2) | 590 bp |

The three fragments overlap substantially and are interchangeable for the present purposes. The 609 bp fragment, extending from −623 to −14 relative to the translation start site (HUMERPA nucleotide positions 2 to 610), is ligated at both ends with ClaI linkers. The resulting ClaI-linked fragment is digested with ClaI and inserted into the ClaI site of pBluescriptIISK/+ (Stratagene), with the orientation such that HUMERPA nucleotide position 610 is adjacent to the SalI site in the plasmid polylinker). This plasmid, p5' EPO, can be cleaved, separately, at the unique FspI or SfiI sites in the EPO upstream fragment (HUMERPA nucleotide positions 150 and 405, respectively) and ligated to the mouse metallotheionein promoter. Typically, the 1.8 kb EcoRI-BglII from the mMT-I gene [containing no mMT coding sequences; Hamer, D. H. and Walling M., *J. Mol. Ap Gen.* 1:273–288 (1982); this fragment can also be isolated by known methods from mouse genomic DNA using PCR primers designed from analysis of mMT sequences available from Genbank; i.e., MUSMTI, MUSMTIP, MUSMTIPRM] is made blunt-ended by known methods and ligated with SfiI digested (also made blunt-ended) or FspI digested p5' EPO. The orientations of resulting clones are analyzed and those in which the former mMT BglII site is proximal to the SalI site in the plasmid polylinker are used for targeting primary and secondary human fibroblasts. This orientation directs mMT transcription towards HUMERPA nucleotide position 610 in the final construct. The resulting plasmids are designated p5' EPO-mMTF and p5' EPO-mMTS for the mMT insertions in the FspI and SfiI sites, respectively.

Additional upstream sequences are useful in cases where it will be desirable to modify, delete and/or replace negative regulatory elements or enhancers that lie upstream of the initial target sequence. In the case of EPO, a negative regulatory element that inhibits EPO expression in extrahepatic and extrarenal tissues [Semenza, G. L. et al., *Mol. Cell. Biol.* 10:930–938 (1990)] can be deleted. A series of deletions within the 6 kb fragment are prepared. The deleted regions may be replaced with an enhancer with broad host-cell activity [e.g. an enhancer from the Cytomegalovirus (CMV)].

The orientation of the 609 bp 5' EPO fragment in the pBluescriptIISK/+vector was chosen since the HUMERPA sequences are preceded on their 5' end by a BamHI (distal) and HindIII site. (proximal). Thus, a 6 kb BamHI-HindIII fragment normally lying upstream of the 609 bp fragment [Semenza, C. L. et al., *Mol. Cell. Biol.* 10:930–938 (1990)] can be isolated from genomic DNA by known methods. For example, a bacteriophage, cosmid, or yeast artificial chromosome library could be screened with the 609 bp PCR amplified fragment as a. probe. The desired clone will have a 6 kb BamHI-HindIII fragment and its identity can be confirmed by comparing its restriction map from a restriction map around the human EPO gene determined by known methods. Alternatively, constructing a restriction map of the human genome upstream of the EPO gene using the 609 bp fragment as a probe can identify enzymes which generate a fragment originating between HUMERPA coordinates 2 and 609 and extending past the upstream BamHI site; this fragment can be isolated by gel electrophoresis from the appropriate digest of human genomic DNA and ligated into a bacterial or yeast cloning vector. The correct clone will hybridize to the 609 bp 5' EPO probe and contain a 6 kb BamHI-HindIII fragment. The isolated 6 kb fragment is inserted in the proper orientation into p5' EPO, p5' EPO-mMTF, or p5' EPO-mMTS (such that the HindIII site is adjacent to HUMERPA nucleotide position 2). Additional upstream sequences can be isolated by known methods, using chromosome walking techniques or by isolation of yeast artificial :chromosomes hybridizing to the 609 bp 5' EPO probe.

The cloning strategies described above allow sequences upstream of EPO to be modified in vitro for subsequent targeted transfection of primary and secondary human fibroblasts. The strategies describe simple insertions of the mMT promoter, as well as deletion of the negative regulatory region, and deletion of the negative regulatory region and replacement with an enhancer with broad host-cell activity.

Example 8

Targeting to Sequences Flanking the Human EPO Gene and Isolation of Targeted Primary and Secondary Human Fibroblasts by Screening For targeting, the plasmids are cut with restriction enzymes that free the insert away from the plasmid backbone. In the case-of p5' EPO-mMTS, HindIII and SalI digestion releases a targeting fragment of 2.4 kb, comprised of the 1.8 kb mMT promoter flanked on the 5' and 3' sides by 405 bp and 204 base pairs, respectively, of DNA for targeting this construct to the regulatory region of the EPO gene. This DNA or the 2.4 kb targeting fragment alone is purified by phenol extraction and ethanol precipitation and transfected into primary or secondary human fibroblasts under the conditions described in Example 4. Transfected cells are plated onto 150 mm dishes in human fibroblast nutrient medium. 48 hours later the cells are plated into 24 well dishes at a density of 10,000 cells/cm [approximately 20,000 cells per well; if targeting occurs at a rate of 1 event per $10^6$ clonable cells (Example 4, then about 50 wells would need to be assayed to isolate a single expressing colony]. Cells in which the transfecting DNA has targeted to the homologous region upstream of EPO will express EPO under the control of the mMT promoter. After 10 days, whole well supernatants are assayed for EPO expression using a commercially available immunoassay kit (Amgen). Clones from wells displaying EPO synthesis are isolated using known methods, typically by assaying fractions of the heterogenous populations of cells separated into individual wells or plates, assaying fractions of these positive wells, and repeating as needed, ultimately isolating the targeted colony by screening 96-well microtiter plates seeded at one cell per well. DNA from entire plate lysates can also be analyzed by PCR for amplification of a fragment using a mMT specific primer in conjunction with a primer lying upstream of HUMERPA nucleotide position 1. This primer pair should amplify a DNA fragment of a size precisely predicted-based on the DNA sequence. Positive plates are trypsinized and replated at successively lower dilutions and the DNA preparation and PCR steps repeated as needed to isolate targeted cells.

Example 9

Targeting to Sequences Flanking the Human EPO Gene and Isolation of Targeted Primary and Secondary Human Fibroblasts by a Positive or a Combined Positive/Negative Selection System The strategy for constructing p5' EPO-mMTF, p5' EPO-mMTS, and derivatives of such with the additional upstream 6 kb BamHI-HindIII fragment can be followed with the additional step of inserting the neo gene adjacent to the mMT promoter. In addition, a negative selection marker, for example, gpt [from pMSG (Pharmacia) or another suitable source], can be inserted adjacent to the HUMERPA sequences in the pBluescriptIISK/+polylinker. In the former case, G418$^r$ colonies are isolated and screened by PCR amplification or restriction enzyme and Southern hybridization analysis of DNA prepared from pools of colonies to identify targeted colonies. In the latter case, G418$^r$ colonies are placed in medium containing 6-thioxanthine to select against the integration of the gpt gene [Besnard, C. et al., *Mol. Cell. Biol.* 7:4139–4141 (1987)]. In addition, the HSV-TK gene can be placed on the opposite side of the insert as gpt, allowing-selection for neo and against both gpt and TK by growing cells in human fibroblast nutrient medium containing 400 µg/ml 9418, 100 µM 6-thioxanthine, and 25 µg/ml gancyclovir. The double negative selection should provide a nearly absolute selection for true targeted events and Southern blot analysis provides an ultimate confirmation.

Example 10

Construction of Targeting Plasmids for Placing the Human Growth Hormone Gene Under the Control of the Mouse Metallothionein Promoter in Primary Human Fibroblasts The following example serves to illustrate one embodiment of the present invention, in which the normal regulatory sequences upstream of the human growth hormone gene are altered to allow expression of human growth hormone in primary or secondary human fibroblast strains.

Targeting molecules similar to those described in Example 7 for targeting to the EPO gene regulatory region are generated using cloned DNA fragments derived from the 5' end of the human growth hormone N gene. An approximately 1.8 kb fragment spanning HUMGHCSA (Genbank Entry) nucleotide positions 3787–5432 (the positions of two EcoNI sites which generate a convenient sized fragment for cloning or for diagnostic digestion of subclones involving this fragment) is amplified by PCR primers designed by analysis of the HUMGHCSA sequence in this region. This region extends from the middle of hGH gene N intron 1 to an upstream position approximately 1.4 kb 5' to the translational start site. pUC12 is digested with EcoRI and BamHI, treated with Klenow to generate blunt ends, and recircularized under dilute conditions, resulting in plasmids which have lost the EcoRI and BamHI sites. This plasmid is designated pUC12XEB. HindIII linkers are ligated onto the amplified hGH. fragment and the resulting fragment is digested with HindIII and ligated to HindIII digested pUC12XEB. The resulting plasmid, pUC12XEB-5' hGH, is digested with EcoRI and BamHI, to remove a 0.5 kb fragment lying immediately upstream of the hGH transcriptional initiation site. The digested DNA is ligated to the 1.8 kb EcoRI-BglII from the mMT-I gene [containing no mMT coding sequences; Hamer, D. H. and Walling, M., *J. Mol. Appl. Gen.*1:273–288 (1982); the fragment can also be isolated by known methods from mouse genomic DNA using PCR primers designed from analysis of mMT sequences available from Genbank; i.e., MUSMTI, MUSMTIP, MUSMTIPRM]. This plasmid p5' hGH-mMT has the mMT promoter flanked on both sides by upstream hGH sequences.

The cloning strategies described above allow sequences upstream of hGH to be modified in vitro for subsequent targeted transfection of primary and secondary human fibroblasts. The strategy described a simple insertion of the mMT promoter. Other strategies can be envisioned, for example, in which an enhancer with broad host-cell specificity is inserted upstream of the inserted mMT sequence.

Example 11

Targeting to Sequences Flanking the Human hGH Gene and Isolation of Targeted Primary and Secondary Human Fibroblasts by Screening For targeting, the plasmids are cut with restriction enzymes that free the insert away from the plasmid backbone. In the case of p5' hGH-mMT, HindIII digestion releases a targeting fragment of 2.9 kb, comprised of the 1.8 kb mMT promoter flanked on the 5' end 3' sides by DNA for targeting this construct to the regulatory region of the hGH gene. This DNA or the,2.9 kb targeting fragment alone is purified by phenol extraction and ethanol precipitation and transfected into primary or secondary human fibroblasts under the conditions described in Example 1. Transfected cells are plated onto 150 mm dishes in human fibroblast nutrient medium. 48 hours later the cells are plated into 24 well dishes at a density of 10,000 cells/cm$^2$ [approximately 20,000 cells per well; if targeting occurs at a rate of 1 event per 10$^6$ clonable cells (Example 4), then about 50 wells would need to be assayed to isolate a single expressing colony]. Cells in which the transfecting DNA has targeted to the homologous region upstream of hGH will express hGH under the control of the mMT promoter. After 10 days, whole well supernatants are assayed for hGH expression using a commercially available immunoassay kit (Nichols). Clones from wells displaying hGH synthesis are isolated using known methods, typically by assaying fractions of the heterogenous populations of cells separated-into individual wells or plates, assaying fractions of these positive wells, and repeating as needed, ultimately isolated the targeted colony by screening 96-well microtiter plates seeded at one cell per well. DNA from entire plate lysates can also be analyzed by PCR for amplification of a fragment using a mMT specific primer in conjunction with a primer lying downstream of HUMGHCSA nucleotide position 5,432. This primer pair should amplify a DNA fragment of a size precisely predicted based on the DNA sequence. Positive plates are trypsinized and replated at successively lower dilutions, and the DNA preparation and PCR steps repeated as needed to isolate targeted cells.

Example 12

Targeting to Sequences Flanking the Human GH Gene and Isolation of Targeted Primary and Secondary Human Fibroblasts by a Positive or a Combined Positive/Negative Selection System The strategy for constructing p5' hGH-mMT can be followed with the additional step of inserting the neo gene adjacent to the mMT promoter. In addition, a negative selection marker, for example, gpt [from pMSG (Pharmacia) or another suitable source], can be inserted adjacent to the HUMGHCSA sequences in the pUC12 polylinker. In the former case, G418$^r$ colonies are isolated and screened by PCR amplification or restriction enzyme and Southern hybridization analysis of DNA prepared from pools of colonies to identify targeted colonies. In the latter case, G418$^r$ colonies are placed in medium containing thioxanthine to select against the integration of the gpt gene [Besnard, C. et al., *Mol. Cell. Biol.* 7:4139–4141 (1987)]. In addition, the HSV-TK gene can be placed on the opposite side of the insert as gpt, allowing selection for neo and against both gpt and TK by growing cells in human fibroblast nutrient medium containing 400 $\mu$g/ml G418, 100 $\mu$M 6-thioxanthine, and-25 $\mu$g/ml gancyclovir. The double negative selection should provide a nearly absolute selection for true targeted events. Southern hybridization analysis is confirmatory.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of producing a therapeutic product in a mammal, said method comprising the steps of:
   a) providing a DNA construct comprising:
      1) exogenous DNA encoding a product to be expressed in a primary or secondary cell of mammalian origin;
      2) DNA sequences homologous with genomic DNA sequences in a primary or secondary cell of mammalian origin; and
      3) DNA sequences encoding a selectable marker;
   b) introducing into a primary or secondary mammalian cell the DNA construct provided in (a), thereby producing a primary or secondary cell comprising the DNA construct provided in (a);
   c) maintaining a primary or secondary cell produced in (b) so that homologous recombination occurs between DNA sequences of said DNA construct that are homologous with genomic DNA sequences of the cell and the genomic DNA sequences of the cell, thereby producing a homologously recombinant primary or secondary cell of mammalian origin having the DNA construct of (a) integrated into genomic DNA of the primary or secondary cell; and
   d) introducing a sufficient number of homologously recombinant primary or secondary cell produced in (c) into a mammal to produce the therapeutic product in the mammal.

2. The method of claim 1, wherein the primary or secondary cell is selected from the group consisting of fibroblasts, keratinocytes, epithelial cells, endothelial cells, glial cells, neural cells, blood cells, muscle cells, hepatocytes, and precursors thereof.

3. The method of claim 1, wherein the primary or secondary cell is a human cell.

4. The method of claim 1, wherein the exogenous DNA encodes a therapeutic product selected from the group consisting of enzymes, cytokines, hormones, antigens, antibodies, clotting factors, regulatory proteins, ribozymes, transcription proteins, receptors, and anti-sense nucleic acid molecules.

5. The method of claim 1, wherein the exogenous DNA is a therapeutic product selected from the group consisting of DNA sequences that sequester a protein or a nucleic acid molecule in the cell, DNA sequences that bind to a cellular regulatory protein, DNA sequences that alter secondary or tertiary chromosomal structure, and DNA sequences that are transcriptional regulatory elements.

6. A method of increasing the efficiency of homologous recombination between (a) genomic DNA sequences of a primary or secondary mammalian cell, and (b) exogenous DNA sequences that are homologous with genomic DNA sequences of the primary or secondary cell, said method comprising stably introducing into the primary or secondary cell a linear DNA construct comprising said exogenous DNA sequences and having a single-stranded overhang at each end, wherein use of said single-stranded overhangs results in increased efficiency of homologous recombination.

7. A method of activating expression of a gene that is present in a primary or secondary cell, but is not expressed or is not expressed at significant levels in the cell as obtained, said method comprising introducing into the cell, by homologous recombination, a DNA construct comprising a regulatory region so that the regulatory region is inserted into or replaces all or a portion of the regulatory region of the gene, and is functionally linked to the gene, thereby producing a homologously recombinant primary or secondary cell in which the gene is expressed.

8. The method of claim 7, wherein the cell is selected from the group consisting of fibroblasts, keratinocytes, epithelial cells, endothelial cells, glial cells, neural cells, blood cells, muscle cells, hepatocytes, and precursors thereof.

9. The method of claim 7, wherein the primary or secondary cell is a human cell.

10. The method of claim 7, wherein the gene encodes a product selected from the group consisting of enzymes, cytokines, hormones, antigens, antibodies, clotting factors, regulatory proteins, transcription proteins, and receptors.

11. The method of claim 7, wherein the gene is selected from the group consisting of the human erythropoietin, growth hormone, and insulin genes.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Homo sapiens

<400> SEQUENCE: 1
agcttctggg cttccagac                                              19

<210> SEQ ID NO 2
<211> LENGTH: 16
<212> TYPE: DNA
<213> ORGANISM: Homo sapiens

<400> SEQUENCE: 2
ggggtccctc agcgac                                                 16

<210> SEQ ID NO 3
<211> LENGTH: 17
<212> TYPE: DNA
<213> ORGANISM: Homo sapiens

<400> SEQUENCE: 3
tgggcttcca gacccag                                                17

<210> SEQ ID NO 4
<211> LENGTH: 20
<212> TYPE: DNA
<213> ORGANISM: Homo sapiens

<400> SEQUENCE: 4
ccagctactt tgcggaactc                                             20
```